United States Patent [19]
Biondi et al.

[11] Patent Number: 5,377,671
[45] Date of Patent: Jan. 3, 1995

[54] CARDIAC SYNCHRONOUS VENTILATION

[75] Inventors: James W. Biondi, North Haven, Conn.; Douglas M. Johnston, Winchester; Stephen J. Herman, Andover, both of Mass.

[73] Assignee: Cardiopulmonary Corporation, Andover, Mass.

[21] Appl. No.: 760,409

[22] Filed: Sep. 16, 1991

Related U.S. Application Data

[63] Continuation-in-part of Ser. No. 692,153, Apr. 26, 1991, abandoned.

[51] Int. Cl.$^6$ .............................................. A61H 31/00
[52] U.S. Cl. .................... 128/204.23; 128/671; 128/700
[58] Field of Search ............... 128/671, 695, 696, 700, 128/725, 28, 30, 30.2, 24 R, 204.23, 204.18, 204.24, 419 G; 600/16, 17; 607/42; 601/1, 6, 11, 152, 149, 148, 151

[56] References Cited
U.S. PATENT DOCUMENTS

| | | | |
|---|---|---|---|
| 2,241,444 | 5/1941 | Bower | 128/30 |
| 2,529,258 | 11/1950 | Lobo | 123/28 |
| 3,212,496 | 10/1965 | Preston | 128/2.06 |
| 3,266,487 | 8/1966 | Watkins et al. | 128/1 |
| 3,303,841 | 2/1967 | Dennis | 128/24 |
| 3,410,263 | 11/1968 | McGinnis | 128/1 |
| 3,426,743 | 2/1969 | Chesnut et al. | 128/1 |
| 3,430,624 | 3/1969 | Flanagan et al. | 128/1 |
| 3,523,529 | 8/1970 | Kissen | 128/2.07 |
| 3,587,562 | 6/1971 | Williams | 128/2.06 |
| 3,730,173 | 5/1973 | Deaton | 128/2.08 |
| 3,750,644 | 8/1973 | Ragsdale | 128/1 D |
| 3,835,845 | 9/1974 | Maher | 128/64 |

(List continued on next page.)

OTHER PUBLICATIONS

Biondi, James W., M.D.; Schulman, D. S., M.D.; and Matthay, R. A., M.D., "Effects of Mechanical Ventilation on Right and Left Ventricular Function," *Clinics in Chest Medicine*, vol. 9, No. 1, Mar. 1988, pp. 55–71.

(List continued on next page.)

*Primary Examiner*—William E. Kamm
*Assistant Examiner*—Kennedy J. Schaetzle
*Attorney, Agent, or Firm*—Weingarten, Schurgin, Gagnebin & Hayes

[57] ABSTRACT

A method and apparatus for providing circulatory and respiratory assistance in a patient. The method includes the steps of determining the onset and duration of at least one portion of the cardiac cycle of the patient and increasing the intrathoracic pressure in the patient by introducing a volume of a respiratory gas into the lungs of the patient during the ventricular systolic portion of the cardiac cycle. The method includes reducing the intrathoracic pressure in the patient by extracting, under either subambient or substantially ambient respiratory gas pressure, a portion of the volume of the respiratory gas from the lungs of the patient, beginning during the diastolic portion of the same cardiac cycle. An apparatus for providing circulatory and respiratory assistance in a patient includes a processing device for determining the onset and duration of at least one portion of the cardiac cycle and a ventilation controller for increasing the intrathoracic pressure in the patient by introducing a volume of a respiratory gas into the lungs of the patient during the ventricular systolic portion of the patient's cardiac cycle and for reducing the intrathoracic pressure in the patient by extracting, under subambient or substantially ambient pressure, a portion of the volume of the respiratory gas from the lungs of the patient beginning during the diastolic portion of the same cardiac cycle.

13 Claims, 2 Drawing Sheets

U.S. PATENT DOCUMENTS

| | | | |
|---|---|---|---|
| 3,923,055 | 12/1975 | Hammacher | 128/145.8 |
| 3,966,358 | 6/1976 | Heimes et al. | 417/12 |
| 3,985,123 | 10/1976 | Herzlinger et al. | 128/2.05 F |
| 4,016,871 | 4/1977 | Schiff | 128/2.06 R |
| 4,077,402 | 3/1978 | Benjamin, Jr. et al. | 128/24 R |
| 4,204,524 | 5/1980 | Martin et al. | 128/1 D |
| 4,316,391 | 2/1982 | Tickner | 73/861.25 |
| 4,397,306 | 8/1983 | Weisfeldt et al. | 128/28 |
| 4,424,806 | 1/1984 | Newman et al. | 128/28 |
| 4,448,192 | 5/1984 | Stawitcke et al. | 128/204.26 |
| 4,509,359 | 4/1985 | Gedeon et al. | 73/23 |
| 4,608,995 | 9/1986 | Linnarsson et al. | 128/713 |
| 4,632,107 | 12/1986 | Butler | 128/204.24 |
| 4,646,733 | 3/1987 | Stroh et al. | 128/207.16 |
| 4,676,232 | 6/1987 | Olsson et al. | 128/28 |
| 4,686,974 | 8/1987 | Sato et al. | 128/204.23 |
| 4,753,226 | 6/1988 | Zheng et al. | 128/64 |

OTHER PUBLICATIONS

Braunwald, Eugene, M.D.; Sonnenblick, E. H., M.D.; and Ross, Jr., J., M.D., "Contraction of the Normal Heart," *Abnormalities of Circulatory Function*, pp. 413–452.

Guimond, Jean-Gilles; Rinsky, M. R., and Matuschak, G. M., "Effect of synchronous increase in intrthoracic pressure on cardiac performance during acute endotoxemia," publ. of *the American Physiological Society*, 0161-7567/90, 1990, pp. 1502–1508.

Matuschak, George M.; Pinsky, M. R., and Klain, M., "Hemodynamic effects of synchronous high-frequency jet ventilation during acute hypovolemia," publ. of *the American Physiological Society*, 0161-7567/86, 1986, pp. 44–53.

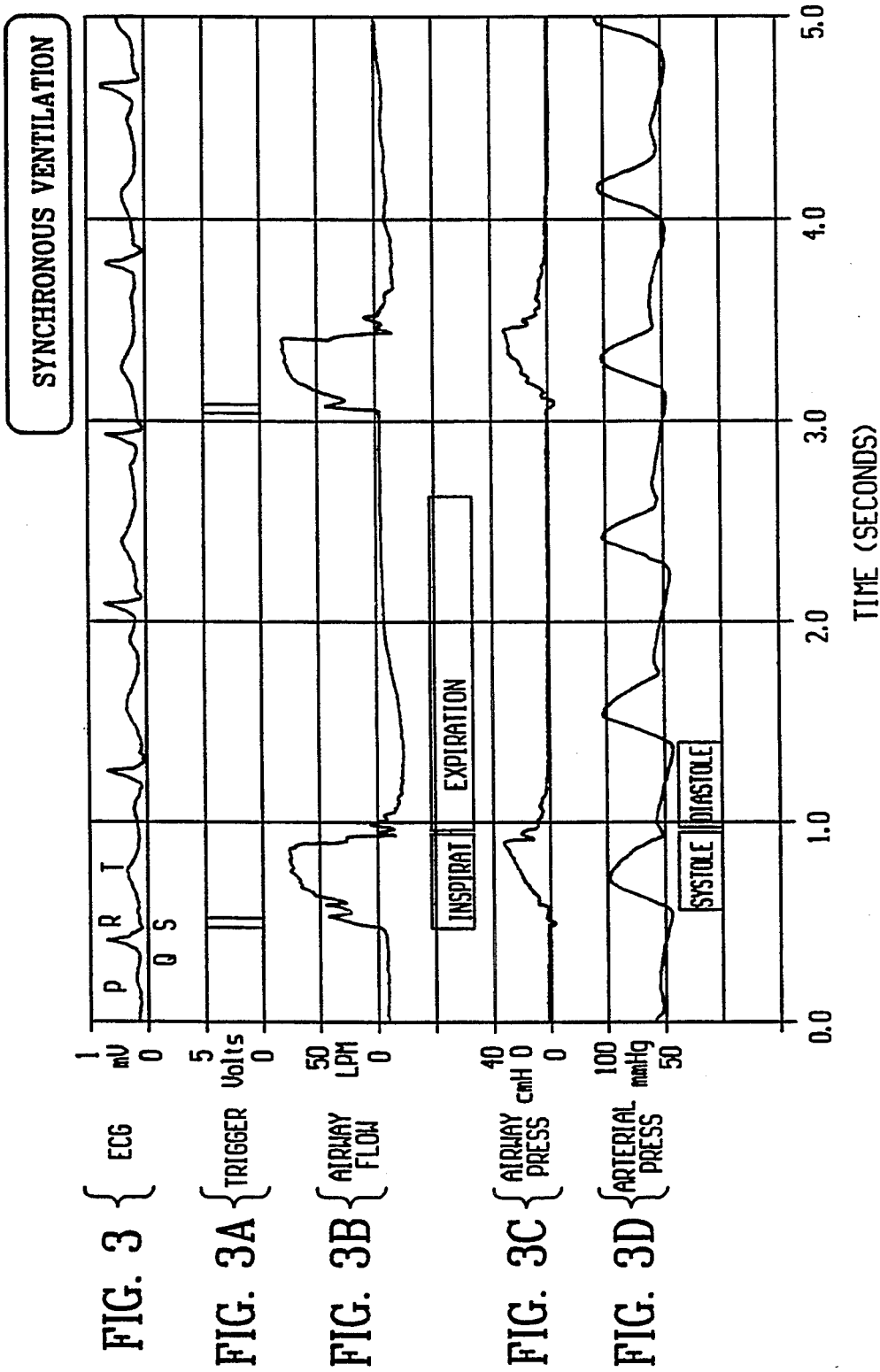

CARDIAC SYNCHRONOUS VENTILATION

RELATED APPLICATION

This application is a continuation-in-part of U.S. patent application Ser. No. 07/692,153, filed Apr. 26, 1991, entitled CIRCULATORY ASSIST METHOD AND APPARATUS, now abandoned, herein incorporated by reference.

FIELD OF THE INVENTION

The invention relates generally to the field of respiratory assist devices and specifically to ventilators.

BACKGROUND OF THE INVENTION

Life support for patients with compromised respiratory function is typically maintained by the periodic introduction and extraction of a respiratory gas by mechanical means. The mechanical means, a ventilator, periodically introduces, under positive pressure, a respiratory gas into a tube inserted into the trachea of the patient. The portion of a mechanical ventilatory cycle during which a respiratory gas is introduced under positive pressure causes the gas to move into and inflate the lungs. Following the portion of the ventilatory cycle during which the respiratory gas is introduced under positive pressure, the ventilator reduces the gas pressure and the lungs deflate, causing the respiratory gas to be passively exhaled. The ventilatory cycle provides the movement of oxygen into the lungs and the removal of carbon dioxide from the lungs necessary to keep the patient alive. Following the portion of the ventilatory cycle during which the respiratory gas is passively exhaled, the portion of the ventilatory cycle during which the respiratory gas is introduced begins again and the cycle is thus repeated.

Although ventilation technology has been known for more than one hundred years, recent advances in control technology using microprocessors have permitted physicians to control a wide range of parameters, such as end exhalation pressure values, tidal and total volume and respiratory gas introduction/extraction times, in order to optimize the patient's respiratory function. However, it has relatively recently been determined that attempts to optimize ventilatory function may result in an unwanted and potentially dangerous interference with cardiac function.

The interference with cardiac function is a result of the heart and the lungs being commonly located within a relatively rigid chest cavity. As positive pressure is applied to the lungs and the lungs expand, they occupy a larger volume within the chest cavity and increase the pressure around the heart and compress the veins returning blood to the heart. This pressure, if applied during the diastolic or filling phase of the cardiac cycle, prevents the heart from filling and ejecting adequately and has been shown to decrease cardiac output by as much as 50%.

Investigators have found however, that if positive pressure is used to inflate the lungs predominantly during the systolic or contraction phase of the cardiac cycle, the external pressure exerted by the lungs on the heart aids in the emptying of the heart and hence improves cardiac output. To use this technique, the investigators have typically utilized ventilatory frequencies which are at, or at a subharmonic of, the heart frequency. The use of a ventilatory frequency which is at the cardiac heart rate frequency results in a ventilatory rate (75-150 breaths per minute) which is much higher than the normal ventilatory rate (10-75 breaths per minute). Such a high frequency of ventilation requires a subnormal tidal volume to be used which, in turn, hinders the maintenance of normal physiological oxygen and carbon dioxide concentrations. In addition, the high frequency rate of ventilation also results in a higher average airway pressure, which can cause lung injury and, in itself, can interfere with the normal mechanism of cardiac filling and ejection.

The present invention relates to a method and apparatus for timing the respiratory gas introduction and extraction portions of the ventilatory cycle so as to be synchronous with portions of the cardiac cycle.

SUMMARY OF THE INVENTION

The invention relates to a method of providing circulatory and respiratory assistance in a patient. The method includes the steps of determining the onset and duration of at least one portion of the cardiac cycle of the patient and increasing the intrathoracic pressure of the patient by introducing a volume of a respiratory gas under a positive pressure into the lungs of the patient during the ventricular systolic portion of the cardiac cycle. Following the introduction of the respiratory gas into the lungs of the patient under a positive pressure, the method includes reducing the pressure of the respiratory gas and hence reducing intrathoracic pressure of the patient. This reduction in pressure is accomplished by extracting, during the diastolic portion of the cardiac cycle, under subambient or substantially ambient pressure, a portion of the volume of the respiratory gas from the lungs.

An apparatus for providing circulatory and respiratory assistance in a patient in conformance with this method includes a processing device for determining the onset and duration of at least one portion of the cardiac cycle and a pressure regulating device for increasing the intrathoracic pressure of the patient by introducing a volume of a respiratory gas into the lungs of the patient during the ventricular systolic portion of the patient's cardiac cycle and for reducing the intrathoracic pressure of the patient by extracting, under subambient or substantially ambient pressure, a portion of the volume of the respiratory gas from the lungs during the diastolic portion of the cardiac cycle. The method and apparatus herein disclosed, provides improved cardiac output while employing a normal physiological breath rate and tidal volume.

BRIEF DESCRIPTION OF THE DRAWINGS

Other features and benefits of the invention can be more clearly understood with reference to the specification and the accompanying drawing in which:

FIG. 3 is a graphical representation of the ECG of a human patient during a clinical trial of the method of the invention;

FIG. 3A is a graphical representation of the trigger pulse generated during the clinical trial of FIG. 3;

FIG. 3B is a graphical representation of the airway flow of the patient measured during the clinical trial of FIG. 3;

FIG. 3C is a graphical representation of the airway pressure delivered to the patient during the clinical trial of FIG. 3; and FIG. 3D is a graphical representation of the arterial pressure measured in the patient during the clinical trial of FIG. 3.

DESCRIPTION OF THE PREFERRED EMBODIMENT

Figure 1:
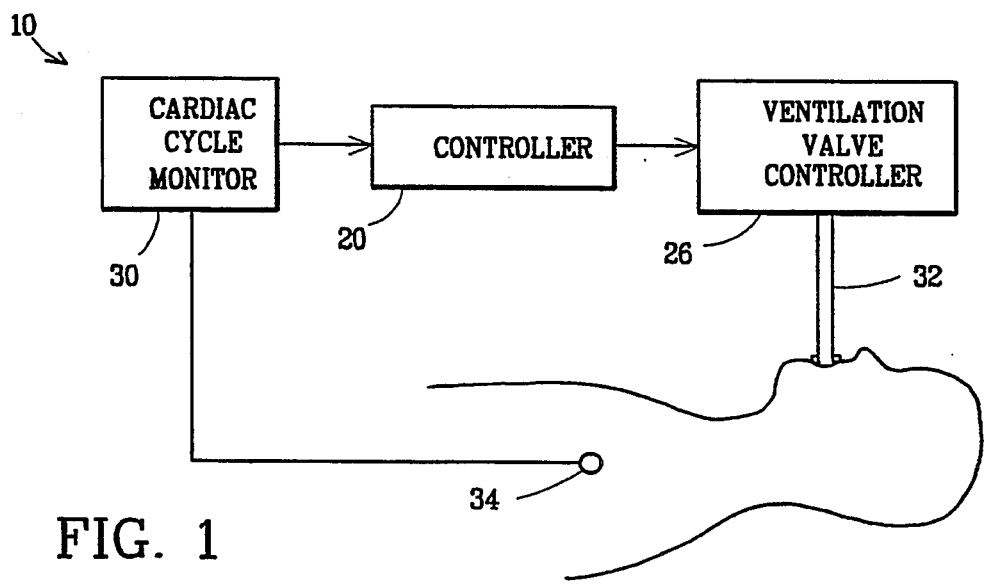
FIG. 1 is a block diagram of an embodiment of the invention.

Referring to FIG. 1, an embodiment of the apparatus 10 includes a master controller 20, a ventilation valve controller 26 (which includes a respiratory gas source, a vacuum source, and pressure and flow sensors which measure the pressure and flow, respectively, of the respiratory gas as supplied to and extracted from the patient) and a cardiac cycle monitor 30. In the embodiment shown, the patient is intubated and the tracheal tube 32 attached to the ventilation valve controller 26. In this embodiment a respiratory gas is introduced and extracted through the tracheal tube 32 under the control of the ventilation valve controller 26. The ventilation valve controller 26 is programmed to introduce a predetermined constant volume of respiratory gas into the patient during a predetermined time interval. The cardiac cycle monitor 30 in one embodiment is an electrocardiogram device which has electrocardiogram leads 34 attached to the patient being monitored. Although in this embodiment, the electrocardiogram device is used to measure the cardiac cycle, other cardiac cycle monitors 30, such as arterial blood pressure monitors, may be used.

The output signal from the cardiac cycle monitor 30 is the input signal to the master controller 20. The master controller 20 analyzes the cardiac cycle signal provided by the cardiac cycle monitor 30 to determine the duration of the various cardiac cycle periods. The master controller 20, based upon the cardiac cycle data, generates a ventilation valve controller control signal.

Figure 2:
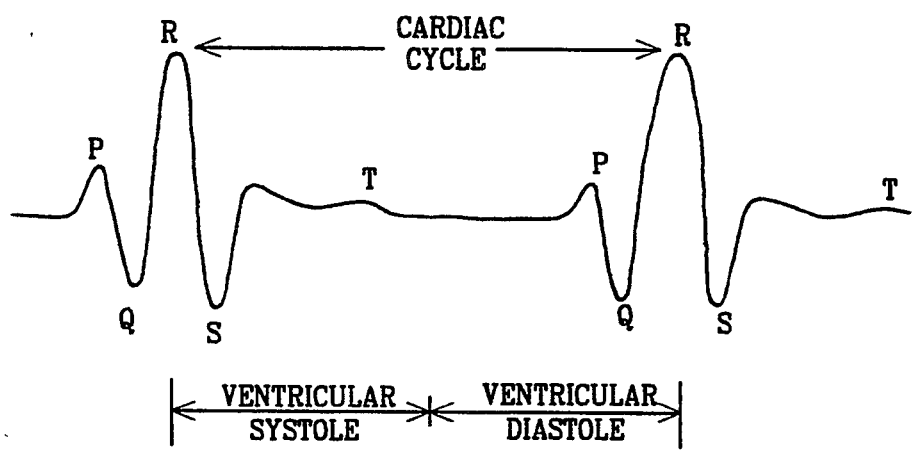
FIG. 2 is a representation of an electrocardiogram.

FIG. 2 depicts two cycles of electrocardiogram waveforms as would be generated by the cardiac cycle monitor 30. An electrocardiogram waveform includes P,Q,R,S and T portions. The difference between the same portion of successive cardiac waveforms defines a cardiac cycle. Ventricular systole begins at the peak of the R portion of the electrocardiogram and ends when the electrocardiogram returns to baseline following the T portion of the electrocardiogram. The remainder of the cardiac cycle is ventricular diastole. In the embodiment shown, which utilizes constant volume ventilation, the clinician sets the desired tidal volume and minute volume as input values to the master controller 20. From these input values, the master controller 20 calculates the breath rate from the relationship breath rate=minute vol./tidal vol.

The output waveform from the cardiac cycle monitor 30 is another input signal to the master controller 20. The master controller 20 generates a control signal for the ventilation controller 26 at the calculated breath rate and synchronized so as to cause the introduction of the respiratory gas to begin during systole. Typically, the tidal volume and timing are selected such that a substantial portion of the tidal volume may be introduced during systole.

The master controller 20 instructs the ventilation controller 26 not only to begin introduction of the respiratory gas during the ventricular systolic portion of the cardiac cycle, but to begin extraction of the respiratory gas during the diastolic portion of the same cardiac cycle. Additionally, the ventilation controller 26 may be programmed by the master controller 26 to produce any of a variety of pressure profiles during respiratory gas introduction and extraction. The ability to begin respiration in the systolic portion of one cardiac cycle and to complete respiratory gas extraction during a subsequent cardiac cycle makes it possible to have a ventilatory rate which is a fraction of the heart rate and thereby decrease the number of breaths per unit time to a more physiological rate.

In another embodiment, the master controller 20 may be programmed instead for pressure support ventilation, in which a predetermined pressure level, rather than a predetermined volume, is delivered to the patient. The clinician sets the pressure support level and the desired breath rate as input values to the master controller 20. In pressure support ventilation the minute volume is variable, depending on the impedance characteristics of the patient's lungs.

The master controller 20 generates a control signal for the ventilation controller 26 at the calculated breath rate and synchronized so as to cause the pressure supplied to the patient to rise to the pressure support level during systole. During the entire period of respiratory gas introduction, the master controller 20 instructs the ventilation controller 26 to maintain the pressure supplied to the patient at the pressure support level. Typically the pressure support level and timing are selected so that a normal physiologic tidal volume may be introduced substantially during systole. The flow of the delivered respiratory gas starts at a maximum rate and then declines as the pressure in the patient's lungs increases. The rate drops to a fixed percentage of the maximum rate, as determined by the master controller 20.

The master controller 20 then instructs the ventilation controller 26 immediately, or after a predetermined time interval, to reduce the pressure of the respiratory gas being supplied to the patient to a predetermined end exhalation pressure level, which may be at, below or above ambient pressure, as determined by the clinician. The respiratory gas is then extracted from the patient. The extraction of the respiratory gas begins during the diastolic portion of the same cardiac cycle, and may continue during subsequent cardiac cycles. The pressure support cycle is then repeated.

A further refinement of both the constant volume ventilation of the first embodiment and the pressure support ventilation of the second embodiment, occurs when the patient begins to regain control of his respiratory function and begins initiating breaths. The ventilator should support those efforts by delivering its controlled breaths coincident with the patient effort. A conflict arises because the patient's efforts are not in synchrony with the cardiac cycle.

To resolve the conflict, yet another embodiment of the invention includes a ventilation controller 26 which detects the onset of an inhalation attempt by the patient as a pressure drop in the portion of the system connected to the tracheal tube 32. In response to this pressure drop, the ventilation controller 26 immediately supplies respiratory gas at a rate sufficient to maintain the pressure of the respiratory gas delivered to the patient at ambient pressure, supplying the flow of gas the patient demands. When the subsequent ventricular systole occurs, the master controller 20 instructs the ventilation controller 26 to either introduce a fixed volume of respiratory gas at an elevated pressure, as previously described with regard to constant volume ventilation, or to supply respiratory gas as a rate sufficient to maintain the pressure delivered to the patient at a pressure support level, as previously described with regard to pressure support ventilation, thus delivering a controlled breath which effectively supports the heart.

FIG. 3 depicts the electrocardiogram (ECG) of a human subject during a clinical trial of the method of the invention utilizing constant volume ventilation. The heart rate of the patient is approximately eighty beats per minute. FIG. 3A depicts the trigger pulse generated by the master controller 20 in response to the ECG. FIG. 3B depicts the flow of respiratory gas into the patient as a result of the respiratory gas pressure FIG. 3C applied to the patient by the ventilator 26. FIG. 3D depicts the arterial pressure measured in the patient.

In this trial, the trigger pulse was set to begin in the first 30% of the systolic portion of the cardiac cycle. This permitted the respiratory gas to begin flowing into the patient between about seventy-five msec. to about one hundred and twenty five msec. after the R peak in the ECG (FIGS. 3, 3B and 3D). In this trial, the respiratory gas pressure was dropped asymptotically to zero at the start of diastole (FIG. 3C). That is to say that introduction of the respiratory gas was substantially completed during systole. The pressure remained substantially at ambient pressure for the next subsequent two heart beats and was increased again during the systolic portion of the third subsequent heartbeat. This corresponds to a ventilatory rate of about twenty-five breaths per minute. Typically, in each of the trials during each ventilatory cycle, at least 5 ml. of respiratory gas per kg. of patient weight was introduced into the patient.

The pressure profile (FIG. 3C) generated by the ventilator, an exponential increase in pressure followed by an exponential decrease in pressure, was selected to correspond to a well known treatment modality for comparison purposes. Therefore, in this trial the ventilatory pressure was not made subambient. That is, forced extraction of the respiratory gas from the lungs did not occur.

Table I compares the percent change in cardiac output as measured by a thermal dilution catheter for a group of five patients between conventional ventilation, as is typically performed in an intensive care unit, and cardiac synchronous ventilation. As can be seen, the change in cardiac output resulting from using the cardiac synchronous ventilation technique of the invention rather than the conventional ventilation technique was significant and resulted in an average 24% improvement. The method therefore permits an increase in venous blood flow to the heart and thereby permits an increase in cardiac output when compared to conventional ventilation techniques.

These and other examples of the concept of the invention illustrated above are intended by way of example and the actual scope of the invention is to be determined solely from the following claims.

What is claimed is:

1. A method of providing circulatory and respiratory assistance in a patient having a cardiac cycle including a ventricular systolic portion and a ventricular diastolic portion, said method comprising the steps of:
    beginning the introduction of said respiratory gas upon the start of an inhalation by said patient;
    determining the onset and duration of at least one said portion of said cardiac cycle;
    increasing the intrathoracic pressure of said patient by introducing a volume of a respiratory gas into the lungs of said patient during said ventricular systolic portion of said cardiac cycle; and
    reducing the intrathoracic pressure of said patient by beginning extracting said volume of said respiratory gas from said lungs of said patient during said diastolic portion of the same cardiac cycle.

2. The method of claim 1 wherein said volume is substantially a tidal volume.

3. The method of claim 1 wherein said step of increasing said intrathoracic pressure occurs by introducing a volume of respiratory gas at a predetermined pressure support level.

4. The method of claim 1 wherein said introduction and said extraction occur at a rate of less than approximately 75 times per minute.

5. The method of claim 1 wherein said volume of respiratory gas introduced is greater than approximately 5 ml per kg of patient weight.

6. The method of claim 1 wherein said extraction occurs under subambient pressure.

7. The method of claim 1 wherein said extraction occurs under substantially ambient pressure.

8. An apparatus for providing circulatory and respiratory assistance in a patient having a cardiac cycle including a ventricular systolic portion and a ventricular diastolic portion, said apparatus comprising:
    a monitoring device for detecting the patient's cardiac cycle;
    a processing device having an input in electrical communication with said monitoring device and an output, said processing device determining the onset and duration of at least one portion of said cardiac cycle and providing at least one control signal on said output in response thereto; and
    a ventilation controller having an input in electrical communication with said output of said processing device, said ventilation controller increasing the intrathoracic pressure of said patient by introducing a volume of a respiratory gas from a source of said gas into the lungs of said patient during said ventricular systolic portion of said patient's cardiac cycle and for reducing the intrathoracic pressure of said patient by extracting a portion of said volume of said respiratory gas from said lungs of said patient during said diastolic portion of said patient's cardiac cycle, said ventilation controller further comprising an inhalation detection device, said ventilation controller beginning the introduction of said respiratory gas upon the start of an inhalation, as detected by said inhalation detection device, by said patient, and prior to the ventricular systolic portion of the cardiac cycle of said patient in response to said at least one control signal of said processing device.

9. The apparatus of claim 8 wherein said volume is a tidal volume.

10. The apparatus of claim 8 wherein said processing device comprises a microprocessor system in communication with said cardiac cycle monitoring device.

11. The apparatus of claim 10 wherein said cardiac cycle monitoring device is an electrocardiogram device.

12. The apparatus of claim 10 wherein said cardiac cycle monitoring device is an arterial blood pressure device.

13. The apparatus of claim 10 wherein said microprocessor system comprises a microprocessor and a set of instructions, said microprocessor for executing said instructions to determine the portions and duration of said cardiac cycle.

* * * * *